United States Patent [19]

Ballard et al.

[11] Patent Number: 5,077,276
[45] Date of Patent: Dec. 31, 1991

[54] GROWTH FACTOR

[75] Inventors: Francis J. Ballard, Glenalla; John C. Wallace, Coromandel Valley; Geoffrey L. Francis, Athelstone; Christopher J. Bagley, Parkside, all of Australia

[73] Assignee: Gropep Pty Ltd, Adelaide, Australia

[21] Appl. No.: 479,183

[22] PCT Filed: Aug. 21, 1986

[86] PCT No.: PCT/AU86/00246

§ 371 Date: Jun. 9, 1987

§ 102(e) Date: Jun. 9, 1987

[87] PCT Pub. No.: WO87/01038

PCT Pub. Date: Feb. 26, 1987

Related U.S. Application Data

[63] Continuation of Ser. No. 61,319.

[51] Int. Cl.$^5$ .................. A61K 37/36; C07K 7/10; C07K 7/40
[52] U.S. Cl. ........................... 514/12; 514/3; 514/21; 530/303; 530/324
[58] Field of Search ............... 530/303, 324, 305, 333, 530/344; 514/3, 12, 21

[56] References Cited

U.S. PATENT DOCUMENTS 4,876,242 10/1989 Applebaum et al. ................ 514/3

FOREIGN PATENT DOCUMENTS 0158892 10/1985 European Pat. Off. .
227619 7/1987 European Pat. Off. .
309050 3/1989 European Pat. Off. .
8500831 2/1985 PCT Int'l Appl. .

OTHER PUBLICATIONS

Sara et al., Proc. Natl. Acad. Sci. USA, vol. 78, No. 5, pp. 3175-3179 (5/81).
Fagerstedt et al., Acta Endocrinol., vol. 103 (256), p. 216, (1983).
Rudinger, Peptide Hormones Parsons (ed.), U Park Press, Baltimore (1976).
Svoboda et al., Biochemistry, vol. 19, pp. 790-797, (1980).
Carlsson-Skwirut et al., FEBS, vol. 201, No. 1, pp. 46-50 (5/1986).
Sara et al, Proc. Natl. Acad. Sci. USA, vol. 83, pp. 4904-4907 (7/1986).
The Merck Index, 10th ed. Nos. 8560, 4354, 7685, 4330, 9229 and 5288, pp. 1246, 645, 1121, 641, 1344 and 782 (1983).
E. Rindernecht et al., J. Biol. Chem., 253, 2769-2776 (1978).
R. B. Merrifield, Angew. Chem. Int. Ed., 24, 799-810 (1985).
F. J. Ballard et al., Biochem. and Biophys. Res. Commun., 149, 398-404, (12/16/87).
Chemical Abstracts, vol. 104, No. 23, Abs. No. 203501c (1986), Blumberg et al.
Chemical Abstracts, vol. 106, No. 13, Abs. No. 96902b (1987), Carlsson-Skwirut et al.
Chemical Abstracts, vol. 108, No. 23, Abs. No. 198502e (1988), Francis et al.
Chemical Abstracts, vol. 108, No. 23, Abs. No. 202006r (1988), Dawe et al.
Chemical Abstracts, vol. 109, No. 3, Abs. No. 17150r (1988), Bayne et al.
Chemical Abstracts, vol. 109, No. 11, Abs. No. 86924h (1988), Cascieri et al.
C. Carlsson-Skwirut et al., Biochim. Biophys. Acta, 1011, 192-197 (1989).
M. Ross et al., Biochem. J., 258, 267-272 (1989).
C. J. Bagley et al., Biochem. J., 259, 665-671 (1989).
Chemical Abstracts, vol. 97, No. 24215c, Nokihara, K. et al., "Synthetic and Immunological Studies on C-domain of Insulin-like Growth Factor (IGF)".

Primary Examiner—John Doll
Assistant Examiner—Christina Chan
Attorney, Agent, or Firm—Merchant, Gould, Smith, Edell, Welter & Schmidt

[57] ABSTRACT

A peptide analogue of mammalian insulin-like growth factor-1 wherein from 1 to 5 amino acid residues are absent from the N-terminal.

10 Claims, 1 Drawing Sheet

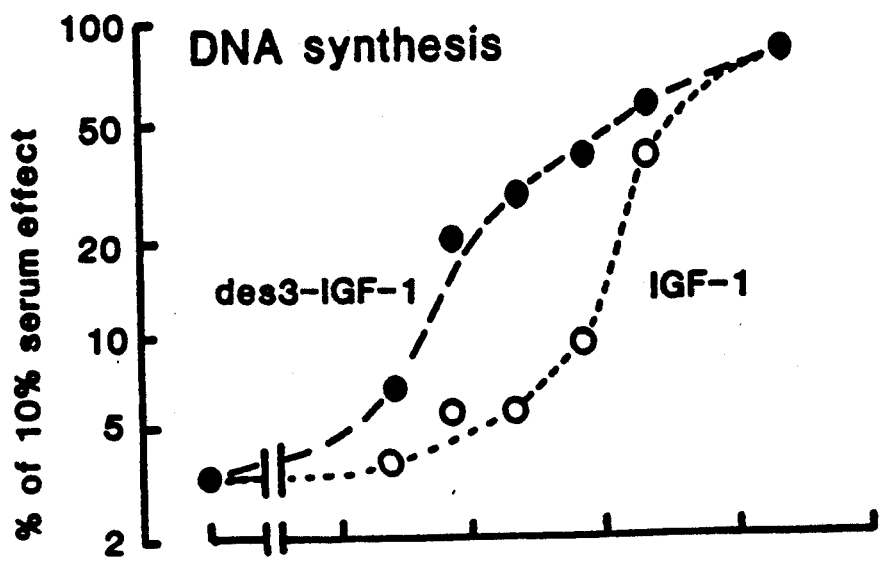
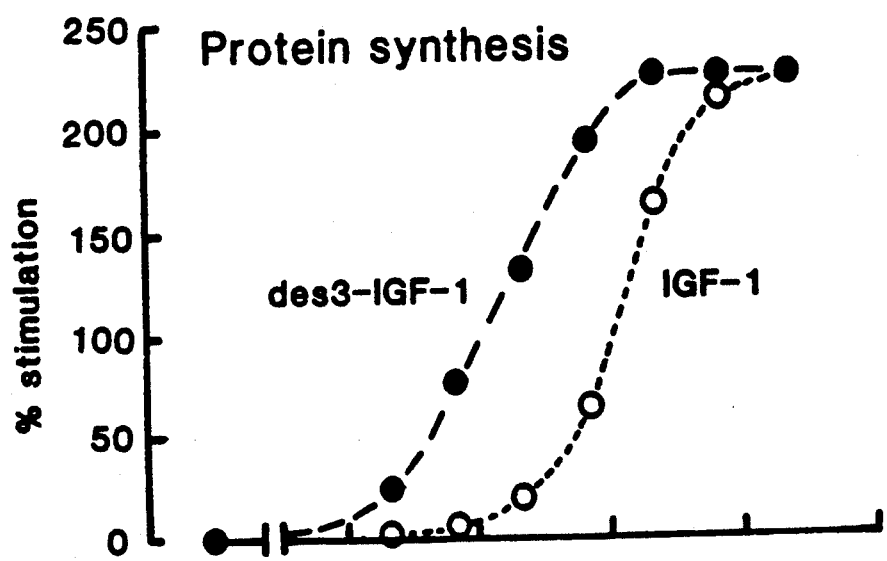
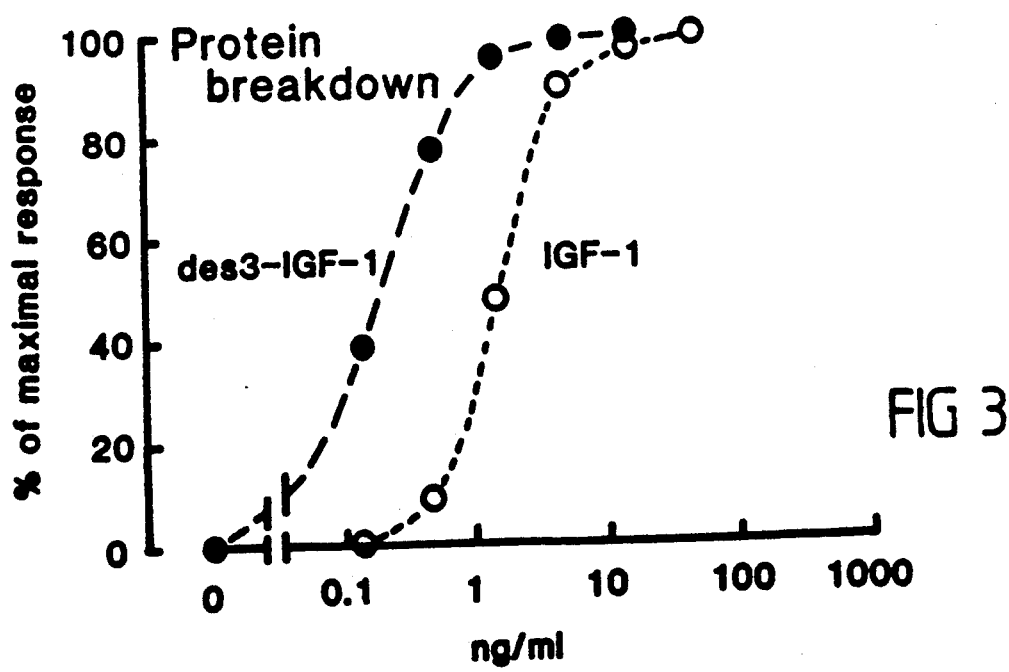

GROWTH FACTOR

This is a continuation of application Ser. No. 061,319, filed 6/9/87, now abandoned.

This invention relates to growth factors, related compounds and their use.

Insulin-like growth factor-1, a somatomedin, is a small protein that has been shown to stimulate growth of a wide range of mammalian cells in culture. Human IGF-1 (hIGF-1) has been purified to homogeneity from human serum and its complete amino acid sequence established. The serum mediator of growth hormone action, somatomedin C, has been shown to have an identical sequence to hIGF-1 so that these two are now considered as being synonymous. The amino acid sequence established for hIGF-1 beginning with the N-terminal glycine is:

Gly—pro—glu—thr—leu—cys—gly—ala—glu—leu—val—asp—ala—leu—gln—phe—val—cys—gly—asp—arg—gly—phe—tyr—phe—asn—lys—pro—thr—gly—tyr—gly—ser—ser—ser—arg—arg—ala—pro—gln—thr—gly—ile—val—asp—glu—cys—cys—phe—arg—ser—cys—asp—leu—arg—arg—leu—glu—met—tyr—cys—ala—pro—leu—lys—pro—ala—lys—ser—ala IGF-1 levels in serum correlate positively with growth rates in boys during adolescence and negatively with the degree of growth hormone deficiency in growth-retarded subjects, and to both growth rate and eventual size in mice transfected with growth hormone genes. These findings, indirectly linking IGF-1 concentrations with growth rates and. supported by more direct evidence that administration of IGF-1 leads to restoration of growth rates in hypopituitary (growth hormone deficient) rats or mice and to increased growth rates in normal mice, have lead to the interpretation that IGF-1 might usefully be applied: (1) in humans to treat growth hormone deficiencies; (2) in farm animals to increase growth rates and enhance food conversion efficiency. It is further suggested, mostly by analogy with research on growth hormone or anabolic steroids, that administration of IGF-1: (3) may suppress the loss of body protein in severe human catabolic states such as following burns, infection or other trauma; (4) may alter the distribution of tissue to increase the muscle content and decrease the fat content in the body.

The result of the above inferences is that there is a commercial demand for IGF-1 for use in animal growth trials and clinical investigations. However, only milligram amounts of hIGF-1, for example, are available by purification of tonnes of human serum protein.

Accordingly, it is an object of the present invention to overcome, or at least alleviate, one or more of the difficulties related to the prior art.

BRIEF DESCRIPTION OF THE DRAWINGS

FIG. 1. Effects of des3-IGF-1 and IGF-1 on DNA synthesis in cultured L6 myoblasts. Values are expressed relative to the percentage stimulation achieved by 10% fetal bovine serum in parallel cultures.

FIG. 2. Effects of des3-IGF-1 and IGF-1 on protein synthesis is cultured L6 myoblasts. Values are expressed as the percentage stimulation above the rate obtained in growth factor-free media.

FIG. 3. Effects of des3-IGF-1 and IGF-1 on protein breakdown in cultured L6 myoblasts. Values are expressed as a percentage of the maximal inhibitory response achieved.

DETAILED DESCRIPTION OF THE INVENTION

Accordingly in a first aspect there is provided a peptide analogue of mammalian insulin-like growth factor-1 wherein from 1 to 5 amino acid residues are absent from the N-terminal, preferably in a biologically pure form.

Preferably, the peptide is a bovine or human insulin-like growth factor-1 analogue.

More preferably, the peptide analogue has an N-terminal structure selected from

Pro-glu-thr-leu-cys-gly-ala-glu-leu-val-asp-ala-leu-gln-phe-val-cys-gly-asp-arg-gly-phe-tyr-phe-asn-lys-pro-thr-gly-, Glu-thr-leu-cys-gly-ala-glu-leu-val-asp-ala-leu-gln-phe-val-cys-gly-asp-arg-gly-phe-tyr-phe-asn-lys-pro-thr-gly-, Thr-leu-cys-gly-ala-glu-leu-val-asp-ala-leu-gln-phe-val-cys-gly-asp-arg-gly-phe-tyr-phe-asn-lys-pro-thr-gly-, Leu-cys-gly-ala-glu-leu-val-asp-ala-leu-gln-phe-val-cys-gly-asp-arg-gly-phe-tyr-phe-asn-lys-pro-thr-gly-, or Cys-gly-ala-glu-leu-val-asp-ala-leu-gln-phe-val-cys-gly-asp-arg-gly-phe-tyr-phe-asn-lys-pro-thr-gly- By the term "biologically pure form" as used herein in the specification and claims we mean a product from which substantially all impurities or contaminants having biological activity have been eliminated.

"Dose-response curves for the compound destripeptide bovine IGF-1 (des3-IGF-1) and bovine IGF-1 (IGF-1) are compared in three separate assays using cultured 16 myoblast cells. These assays are (FIG. 1) stimulation of DNA synthesis, (FIG. 2) stimulation of protein synthesis, and (FIG. 3) inhibition of protein breakdown. The peptides are added at the indicated concentrations to Eagle's Minimal Essential Medium at the beginning of the respective measurement periods."

It has been discovered that compounds corresponding to IGF-1 but lacking one to five, preferably three amino acid residues from the N-terminal of the molecule can exhibit a substantial increase in biological potency compared with the more complete compounds.

For example, the compound destripeptide bIGF-1 having the formula of bovine IGF-1 (bIGF-1) but lacking the amino acid residues gly, pro and glu from the N-terminal, is effective in inhibiting protein breakdown and stimulating both protein synthesis and DNA synthesis in cellular systems at concentrations between 4 and 50-fold lower than required for entire bIGF-1 or hIGF-1.

For IGF-1 peptides having N-terminal amino acid sequences in common with that of hIGF-1 the elimination of between 1 and 5 amino acid residues from the N-terminal also results in enhanced biological potencies. The said N-terminal amino acid sequence is a feature of the IGF-1 of human, bovine, rat and other mammalian species.

Accordingly in its broadest aspect this invention provides peptide analogues effective in promoting DNA and protein synthesis as well as suppressing protein loss in mammals.

The peptide analogues, including destripeptide IGF-1 and related peptides of this invention are seen as suitable replacements for IGF-1 in the following applications: (1) in human subjects as treatment for growth deficiencies as well as to restrict negative nitrogen balance associated with catabolic conditions; (2) in pituitary normal animals to promote their growth and improve food conversion efficiency.

More specifically, the destripeptide IGF-1 and related peptides may be administered to promote growth and improve food conversion efficiency in economic, warm-blooded animals, including cattle, sheep, pigs and chickens. The modified IGF-1 may be administered alone or with various diluents, carriers or excipients that have been chosen with respect to the intended method of administration.

Accordingly, in a further aspect, the present invention provides a pharmaceutical or veterinary composition for the treatment of protein accumulation deficiencies or protein loss in mammals including (a) an effective amount of a peptide analogue of mammalian insulin-like growth factor-1 wherein from 1 to 5 amino acid residues are absent from the N-terminal; and (b) a pharmaceutically or veterinarilly acceptable diluent, carrier or excipient therefor.

In a further prepared form the present invention provides a composition wherein the peptide analogue is present in amounts sufficient to provide a dose rate of approximately 1 to 1000, preferably 10 to 100 micrograms/kg body weight/day. The peptide analogue may be present, in a unit dosage form, amounts of from approximately 0.02 to 2000 milligrams.

Slow-release, pellet implants would be the preferred method of administration to animals of economic importance as applied in conventional practice.

Accordingly in a still further aspect of the present invention, there is provided a method for the treatment of protein accumulation deficiencies in mammals which method administering to a patient to be treated an effective amount of a peptide analogue of mammalian insulin-like growth factor-1 wherein from 1 to 5 amino acid residues are absent from the N-terminal. The treatment may also be applied to protein loss in mammals.

The peptide analogues, including destripeptide IGF-1 and related peptides of the present invention may be administered to human subjects as a treatment for chronic growth disorders including growth hormone deficiency and somatomedin deficiencies. The modified IGF-1 peptides may be administered parenterally for this purpose, or using procedures outlined above for use with economic animals.

The peptide analogues may be administered to human subjects as a treatment for disorders associated with insufficient growth or tissue wasting including, but not limited to, cancer, cystic fibrosis, Duchenne muscular dystophy, Becker dystrophy, autosomal recessive dystrophy, polymyositis as well as other myopathies. The modified IGF-1 peptides may be administered using procedures given above for growth disorders.

The peptide analogues, including destripeptide IGF-1 and related peptides of this invention may be administered to human subjects as a treatment for acute conditions associated with poor nitrogen status including, but not limited to, burns, skeletal trauma and infection. Although the preferred method of administration may be via addition to parenteral fluids in these critical care situations, other procedures such as those listed above for growth disorders may be appropriate.

The peptide analogues of the present invention may be administered to premature or other human infants to promote growth, improve nitrogen status and to treat catabolic disorders. The peptides may be administered as outlined above for acute human conditions or by enteral routes.

The dose rates and times for the administration of destripeptide IGF-1 and related peptides may be set at levels proportionally less than for full IGF-1 peptides in accordance with the increased potency of the present invention. Dose rates of approximately 1 to 1000 micrograms/kilogram/day may be used. Dose rates of approximately 10 to 100 micrograms/kilogram/day are preferred.

In a further aspect of the present invention there is provided a method for the preparation of a peptide analogue of mammalian insulin-like growth factor-1 wherein from 1 to 5 amino acid residues are absent from the N-terminal which

| method includes | (i) providing a peptide analogue having an N—terminal structure of M—leu—cys—gly—ala—glu—leu—val— asp—ala—leu—gln—phe—val—cys—gly— asp—arg—gly—phe—tyr—phe—asn—lys— pro—thr—gly— wherein M is Gly—pro— glu—thr or Thr— |
|---|---|
| and | (ii) subjecting the peptide analogue to one or more amino acid cleavage steps. |

The peptide analogues can be produced by appropriate modifications to methods existing for the production of the full hIGF-1 peptide. These modifications would be familiar to those familiar with the art.

Specifically, destripeptide human IGF-1 may be synthesised chemically using procedures developed for human IGF-1 (for example: Li et al., Proc Natl. Acad. Sci USA 80: 2216-2220, 1983) but with the final three cycles of amino acid ligation omitted. Likewise, related peptides with between 1 and 5 amino acids omitted from the N-terminus may be obtained. Synthetic destripeptide bovine, ovine or porcine IGF-1 and related peptides may be produced by techniques similar to those used for human IGF-1 using amino acid sequence information for these peptides.

In accordance with the present invention, destripeptide IGF-1 and related peptides may also be produced following transformation of susceptible bacterial, yeast or tissue culture cell hosts with recombinant plasmids that include DNA sequences capable of directing the expression of destripeptide IGF-1 and related peptides. The DNA sequence may be synthetic, chromosomal, cDNA or combinations thereof. The inserted coding sequences may incorporate deletions or omissions to account for differences between the sequence of destripeptide IGF-1 (and related peptides) and the full IGF-1 peptide.

Alternatively, the inserted coding sequences for complete IGF-1 may be used to express the complete IGF-1 peptide chain and the three N-terminal amino acids may be cleaved as part of the down-stream processing. Similar procedures resulting in the production of IGF-1 peptides with between 1 and 5 N-terminal amino acids removed are also in accordance with the present invention.

In a preferred form the present invention provides a method for the preparation of a peptide analogue, destripeptide bovine insulin-like growth factor-1 (bIGF-1) which method includes (i) providing (a) a bovine product selected from colostrum or serum (b) a source of acid (ii) treating the bovine product with an acid sufficient to effect protein extraction.

(iii) subjecting the protein extract to at least one chromatographic solvent elution step to isolate the destripeptide analogue bIGF-1.

Preferably the acid is acetic acid and the solvent is acetonitrile.

More preferably the starting material is bovine colostrum. A liquid chromatography process may be used. A HPLC process may be used. Preferably protein extract is subjected to up to four chromatographic solvent elution steps.

Alternatively or in addition a gel permeation chromatography step may be included.

The present invention will now be more fully described with reference to the accompanying examples. It should be understood, however, that the following description is illustrative only and should not be taken in any was as a restriction on the generality of the description foregoing.

EXAMPLE 1

Destripeptide bIGF-1 may be isolated from bovine colostrum by the following sequential steps, where fractions with bioactivity were combined and applied to the next step:

Acid extraction

Approximately 4 liters of colostrum were centrifuged at 20,000 g for 30 min at 5° C. The infranatant (3.6 liters) was adjusted to pH 2.8 with glacial acetic acid over a period of 1 hour while stirring vigorously at 2° C. The mixture was diluted with 3.6 liters of 1 M acetic acid containing 0.25 M NaCl and stirred for 16 hours at 2° C. Centrifugation at 20,000 g for 30 min at 5° C. yielded an opalescent extract (6 liters).

Chromatography on SP-SEPHADEX C-25 Sulphopropyl Cation-Exchange Resin

One hundred grams of SP-SEPHADEX C-25 sulphopropyl cation-exchange resin were hydrated with water at 95° for 2 h and converted to the hydrogen form by treatment with acetic acid at pH 2.5. The pH 2.8 colostrum extract was added to the gel layer and the mixture stirred overnight at 2°. The gel was slurried into a glass column and washed with 1.5 liter of 1 M acetic acid and subsequently with 50 mM ammonium acetate, pH 5.5 at a flow rate of 50 ml per min until the A280 (5 mm light path) was below 0.05. Elution of bioactivity was achieved with a 500 ml linear gradient from the pH 5.5 buffer to 0.25 M NH4OH containing 0.5 M NaCl, followed by a further 2 liters of the latter solution.

Concentration by C18 reversed-phase chromatography

The eluate from SP-SEPHADEX C-25 sulphopropyl cation-exchange resin chromatography was adjusted to 0.1% with trifluoroacetic acid and the pH to 2.1 with concentrated HCl before adding acetonitrile (10% v/v). This mixture was stirred for 15 h at 2° C. and the precipitate removed by centrifugation at 20,000 g for 30 min. All subsequent steps were carried out at 22° C. The supernatant was pumped through a 12 gram Amicon C18 matrix column previously equilibrated with 0.1% trifluoroacetic acid using a flow rate of 15 ml per min. Elution was accomplished with 0.1% trifluoroacetic acid containing 50% (v/v) of acetonitrile.

Acid-gel permeation

The C18 eluate was freeze dried, dissolved in 75 ml of 1 M acetic acid and pumped on to a 5×90 cm column of TSK FRACTOGEL H55(S) gel-filtration resin equilibrated with 1 M acetic acid. The flow rate was 2 ml per min.

First HPLC Step

The active fractions from the acid-gel permeation column were diluted with 0.12% heptafluorobutyric acid to reduce the acetonitrile concentration to 20% (v/v) and pumped on to an AMICON C18 reversed phase column (22×300 mm), previously equilibrated with the same solution. Protein was eluted at a flow rate of 5 ml per minute, with a 10 min linear gradient to 35% (v/v) acetonitrile followed by a 210 min linear gradient to 56% (v/v) acetonitrile with the counterion maintained at 0.13%.

Second HPLC step

The pool of active fractions was diluted to 20% (v/v) acetonitrile with 0.1% trifluoroacetic acid and pumped onto a WATERS μBONDAPAK C18 reversed phase column (7.8×300 mm) which had previously been equilibrated with 20 (v/v) of acetonitrile in 0.1% trifluoroacetic acid. The flow rate was 1.5 ml per min during loading and 1 ml per min during elution. A three step linear gradient with break points at 29%, 39.8% and 65% (v/v) acetonitrile in 0.1% trifluoroacetic acid was applied over 174 min.

Third HPLC step

The pooled fractions were diluted with 0.5 volumes of 0.1% trifluoroacetic acid and applied to a WATERS NOVAPAK C18 reversed phase RADIAL PAK CARTRIDGE (4 μm, 8×100 mm) previously equilibrated with 10% (v/v) propan-1-ol in 0.1% trifluoroacetic acid. The elution program at a flow rate of 1 ml per min involved a 10 min linear gradient to 16.3% (v/v) propan-1-ol followed by a 157 min linear gradient to 19.8% (v/v) propan-1-ol followed by a 15 min linear gradient to 45% (v/v) propan-1-ol, and a 10 min linear gradient to 62.5 (v/v) propan-1-ol.

Fourth HPLC step

The pooled fractions were diluted with 0.5 volumes of 0.13% heptafluorobutyric acid and injected on to the same column used for the third HPLC step, but equilibrated with 10% (v/v) propan-1-ol in 0.13% heptafluorobutyric acid. The flow rate during elution was 1 ml per min and the program included a 10 min linear gradient to 27.5% (v/v) propan-1-ol followed by a 130 min linear gradient to 41.5% (v/v) propan-1-ol with the counter ion maintained at 0.13%.

Two regions of bioactivity are obtained in pure form after the fourth HPLC step with both:

1. Able to compete effectively with $^{125}$I-labelled human IGF-1 for binding to human placental membranes;
2. Able to compete with $^{125}$I-labelled human IGF-2 for binding to sheep placental membranes;
3. Able to complete with $^{125}$I-labelled human IGF-1 for binding to polyclonal or monoclonal antibodies directed against human IGF-1.

Analysis of the two regions of bioactivity from the fourth HPLC step after S-carboxymethylation by gas-phase sequencing gave the following sequences from the N-terminal:

first eluted peak

Gly-pro-glu-thr-leu-cys-gly-ala-glu-leu-val-asp-ala-leu-gln-phe-val-cys-gly-asp-arg-gly-phe-tyr-phe-asn-lys-pro-thr-glysecond eluted peak Thr-leu-cys-gly-ala-glu-leu-val-asp-ala-leu-gln-phe-val-cys-gly-asp-arg-gly-phe-tyr-phe-asn-lys-pro-thr-gly-tyr-gly-ser- The first sequence is identical to the N-terminal 30 amino acids of human IGF-1 and is clearly, therefore, bovine IGF-1. The sequence of the second peak peptide is again identical to the N-terminal region of hIGF-1 with the exception that the first three amino acids (gly, pro, glu) are absent. This material is referred to, therefore, as destripeptide bIGF-1.

Bioassays of both peaks eluted from the fourth HPLC step have been compared with pure human IGF-1. The assays involve effects on the incorporation of $^3$H-labelled leucine into total cell protein, incorporation of $^3$H-thymidine into cell DNA and the release of $^3$H-labelled leucine, from prelabelled cell protein.

These measurements in rat L6 myoblasts displayed in FIGS. 1, 2 and 3 as dose response curves show that destripeptide bIGF-1 (des3-bIGF-1) is effective at concentrations that average one order of magnitude less than bIGF-1. Even greater differences in potency occur for the stimulation of DNA synthesis or the inhibition of protein breakdown in human lung fibroblasts (see table).

Relative potencies of destripeptide - bIGF-1 (des3-bIGF-1) and bIGF-1 in L6 Myoblasts and human lung fibroblasts [HE(39)L]

| Cell | Measurement | growth factor (ng/ml) | |
|---|---|---|---|
| | | des3-bIGF-1 | IGF-1 |
| L6 | DNA synthesis, 100% stimulation | 0.45 | 5.3 |
| | Protein synthesis, 100% stimulation | 1.6 | 14 |
| | Protein breakdown, half-max inhibition | 0.2 | 1.5 |
| HE(39)L | DNA synthesis, 100% stimulation | 0.15 | 5.3 |
| | Protein breakdown, half-max inhibition | 0.15 | 3.8 |

EXAMPLE 2

Synthesis of IGF-1 peptides

Chemical synthesis of hIGF-1 peptides with between 1 and 5 amino acids eliminated from the N-terminal has been effected by the following procedure.

The starting material was Boc-ala-phenylacetamidomethyl resin. Coupling was effected in an Applied Biosystems Inc model 430A peptide synthesiser with preformed symmetric anhydrides of the Boc-aminoacids in dichloromethane except for the derivatives of arginine, asparagine and glutamine which were coupled in dimethyl formamide (DMF). In all cases a second coupling was performed in DMF. Samples of resin were removed after each cycle of synthesis and subjected to quantitive ninhydrin analysis (Sarin, V. K., Kent, S. B. H., Tam, J. P., Merrifield, R. B.; Anal. Biochem. 17 147-157 (1981). Preview sequence analysis of the side-chain protected, resin-bound peptide was also carried out and together, these indicated an average repetitive yield of 99%.

Portions of resin containing side-chain protected peptides corresponding to the complete sequence of hIGF-1 but with 5 to 1 amino acids not coupled at the N-terminal were removed. Peptides were cleaved and deprotected according to Applied Biosystems Inc procedures and recovered as ether precipitates.

Peptides were redissolved in 6M guanidine hydrochloride pH 8.5 with Tris containing 10 mM dithioerythritol and desalted by reverse phase HPLC and dried. Oxidation of the reduced peptide was effected by dissolving in 50 mM Tris pH 8.5 containing 1 mM reduced glutathione and 0.1 mM oxidised glutathione and incubated at 20° C. for 15 hours. After desalting by reverse phase HPLC samples were dried prior to resuspension. Biological activity was confirmed by the ability of the peptide to stimulate protein synthesis in L6 myoblasts.

It will be appreciated that various modifications and/or alterations may be introduced into the constructions and arrangements of parts previously described without departing from the spirit or ambit of the present invention.

The claims defining the invention are as follows:

1. A peptide analogue of bovine or human insulin-like growth factor-1 having the structure:

X-tyr-gly-ser-ser-ser-arg-arg-ala-pro-gln-thr-gly-ile-val-asp-glu-cys-cys-phe-arg-ser-cys-asp-leu-arg-arg-leu-glu-met-tyr-cys-ala-pro-leu-lys-pro-ala-lys-ser-ala wherein X is the N-terminal structure:

Thr-leu-cys-gly-ala-glu-leu-val-asp-ala-leu-gln-phe-val-cys-gly-asp-arg-gly-phe-tyr-phe-asn-lys-pro-thr-gly.

2. A peptide analogue according to claim 1 in a biologically pure form.

3. A pharmaceutical or vertinary composition for the treatment of protein accumulation deficiencies or protein loss in mammals including:
   (a) an effective amount of a peptide analogue of bovine or human insulin-like growth factor-1 having the structure:

X-tyr-gly-ser-ser-ser-arg-arg-ala-pro-gln-thr-gly-ile-val-asp-glu-cys-cys-phe-arg-ser-cys-asp-leu-arg-arg-leu-glu-met-tyr-cys-ala-pro-leu-lys-pro-ala-lys-ser-ala wherein X is the N-terminal structure:

Thr-leu-cys-gly-ala-glu-leu-val-asp-ala-leu-gln-phe-val-cys-gly-asp-arg-gly-phe-tyr-phe-asn-lys-pro-thr-gly; and (b) a pharmaceutically or venterinarilly acceptable diluent, carrier or excipient therefor.

4. A composition according to claim 3 wherein the peptide analogue is present in amounts of from approximately 0.02 to 2000 milligrams.

5. A method for the treatment of protein accumulation deficiencies in mammals which method includes administering to a mammal to be treated an effective amount of a peptide analogue of bovine or human insulin-like growth factor-1 having the structure:

X-tyr-gly-ser-ser-ser-arg-arg-ala-pro-gln-thr-gly-ile-val-asp-glu-cys-cys-phe-arg-ser-cys-asp-leu-arg-arg-leu-glu-met-tyr-cys-ala-pro-leu-lys-pro-ala-lys-ser-ala wherein X is the N-terminal structure:

Thr-leu-cys-gly-ala-glu-leu-val-asp-ala-leu-gln-phe-val-cys-gly-asp-arg-gly-phe-tyr-phe-asn-lys-pro-thr-gly.

6. A method according to claim 5 wherein the protein accumulation deficiencies to be treated are those which are associated with cancer, cystic fibrosis, Duchenne muscular dystrophy, Becker dystrophy, autosomal recessive dystrophy, polymyositis, or other myopathies.

7. A method according to claim 5 wherein the peptide analogue is administered at a dose rate of approximately 1 to 1000 microgram/kg bodyweight/day.

8. A method for the treatment of protein loss in mammals which method includes administering to a mammal to be treated an effective amount of a peptide analogue of bovine or human insulin-like growth factor-1 having the structure:

X-try-gly-ser-ser-ser-arg-arg-ala-pro-gln-thr-gly-ile-val-asp-glu-cys-cys-phe-arg-ser-cys-asp-leu-arg-arg-leu-glu-met-tyr-cys-ala-pro-leu-lys-pro-ala-lys-ser-ala wherein X is the N-terminal structure:
Thr-leu-cys-gly-ala-glu-leu-val-asp-ala-leu-gln-phe-val-cys-gly-asp-arg-gly-phe-tyr-phe-asn-lys-pro-thr-gly.

9. A method according to claim 8 wherein the protein loss is related to burns, skeletal trauma or infection.

10. A method according to claim 8 wherein the peptide analogue is administered at a dose rate of approximately 1 to 1000 microgram/kg bodyweight/day.

* * * * *